(12) United States Patent
Gardon-Mollard

(10) Patent No.: US 6,572,574 B2
(45) Date of Patent: Jun. 3, 2003

(54) COMPRESSIVE ORTHOSIS OF THE SOCK TYPE FOR TREATING CIRCULATORY DISEASE OF THE LOWER LIMBS, IN PARTICULAR FOR APPLYING COMPRESSIVE SUPPORT TO THE LEG AFTER A VENOUS ULCER

(75) Inventor: Christian Gardon-Mollard, Chamalieres (FR)

(73) Assignee: Innothera Topic International, Société anonyme, Arcueil (FR)

( * ) Notice: Subject to any disclaimer, the term of this patent is extended or adjusted under 35 U.S.C. 154(b) by 0 days.

(21) Appl. No.: 09/986,009

(22) Filed: Nov. 7, 2001

(65) Prior Publication Data

US 2002/0029012 A1 Mar. 7, 2002

Related U.S. Application Data

(63) Continuation of application No. 09/202,361, filed as application No. PCT/FR97/01067 on Jun. 13, 1997.

(30) Foreign Application Priority Data

Jun. 14, 1996 (FR) .............................................. 96 07397

(51) Int. Cl.⁷ ................................................. A61F 13/00
(52) U.S. Cl. .............................. 602/62; 602/63; 602/75
(58) Field of Search .............................. 602/27, 62, 63, 602/65, 75; 2/22

(56) References Cited

U.S. PATENT DOCUMENTS

| 3,386,270 | A |   | 6/1968 | Simmons |
| 3,889,494 | A |   | 6/1975 | Patience et al. |
| 4,086,790 | A |   | 5/1978 | Hanrahan et al. |
| 4,513,740 | A | * | 4/1985 | Westlake ..................... 602/62 |
| 5,185,000 | A | * | 2/1993 | Brandt et al. |

FOREIGN PATENT DOCUMENTS

| DE | 2843991  | 4/1980 |
| DE | 19503459 | 5/1996 |
| EP | 0071818  | 2/1983 |
| FR | 2635001  | 2/1990 |
| GB | 1445233  | 8/1976 |

* cited by examiner

Primary Examiner—Nicholas D. Lucchesi
Assistant Examiner—Lalita M Hamilton
(74) Attorney, Agent, or Firm—Jacobson Holman PLLC

(57) ABSTRACT

The orthosis (1) is designed to apply degressive compression to all or part of the leg starting from the ankle The orthosis has a knitted compressive tubular portion (2) of varying section formed by a leg portion of an elastic stocking that does not have a foot or a heel, said compressive tubular portion being extended at its bottom end by a knitted non-compressive tubular portion (3) suitable for covering at least a portion of the foot, without compressing it, and made for example using a stitch of the plain moss type.

6 Claims, 3 Drawing Sheets

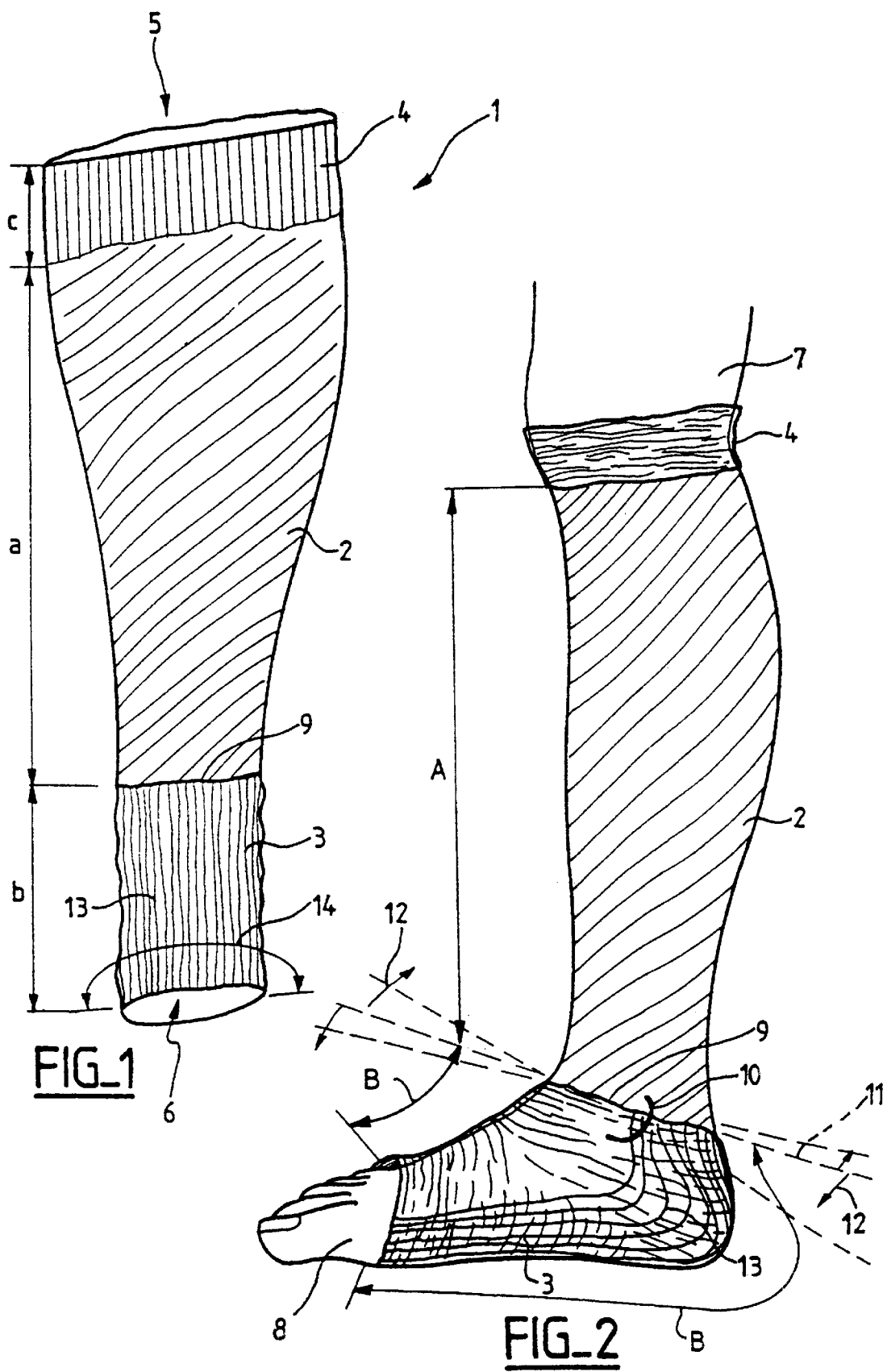

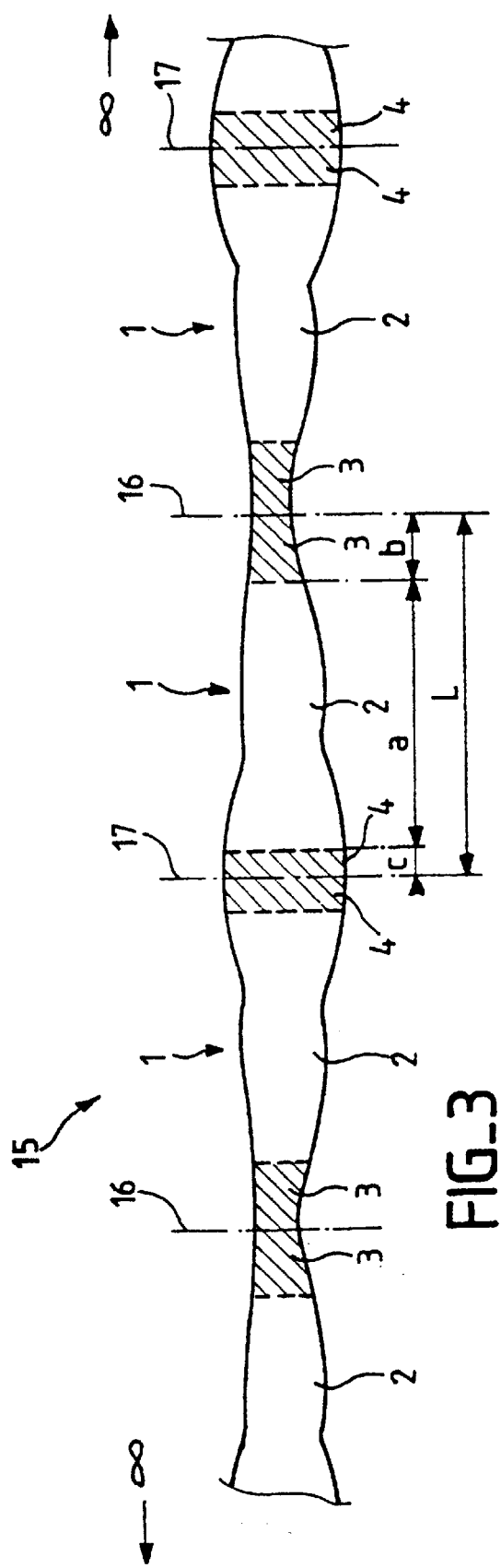
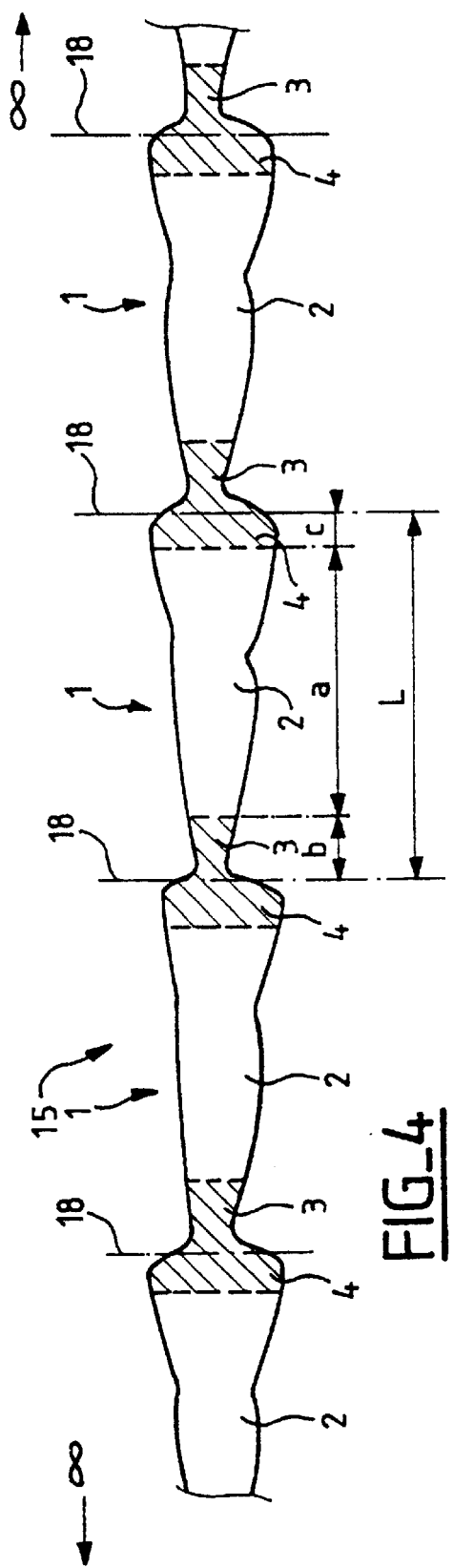

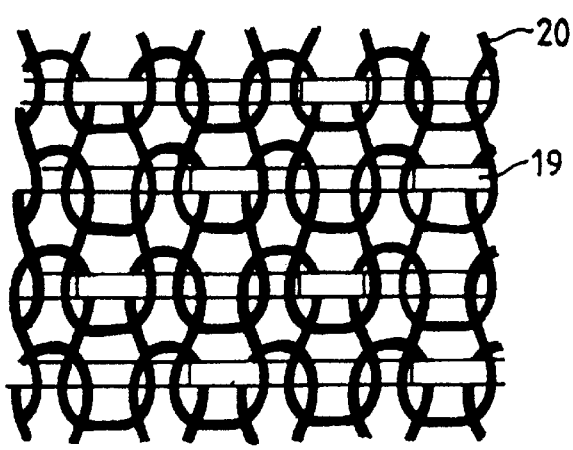
FIG_5
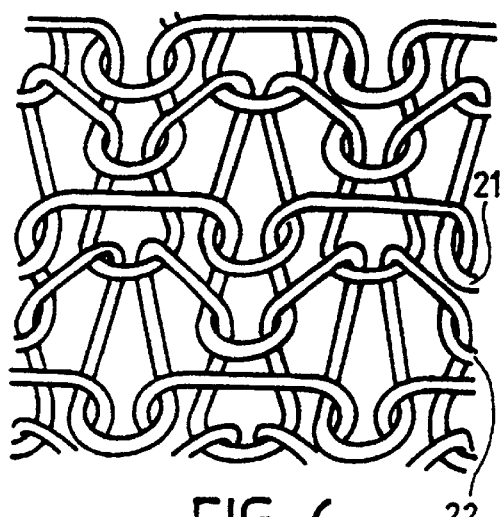
FIG_6
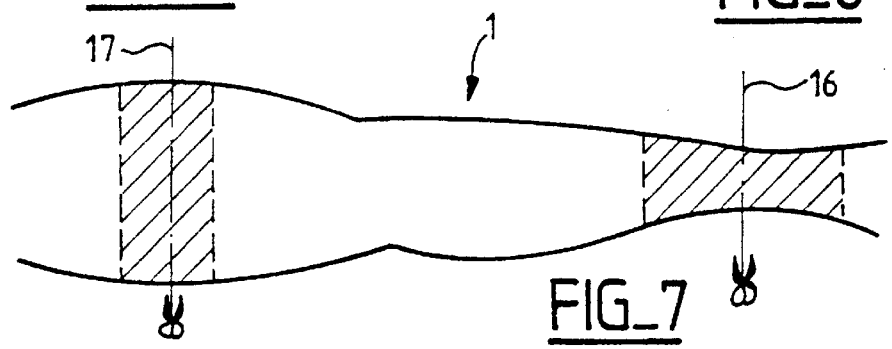
FIG_7
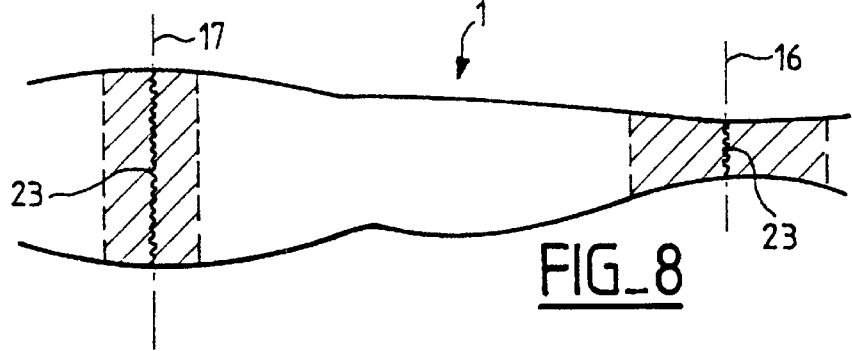
FIG_8
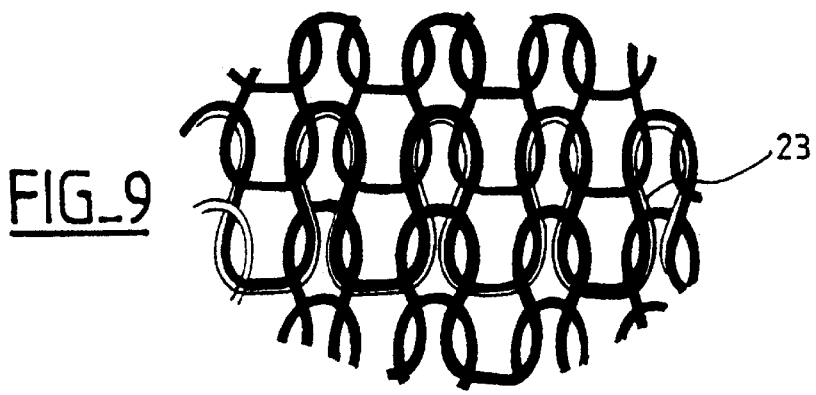
FIG_9

COMPRESSIVE ORTHOSIS OF THE SOCK TYPE FOR TREATING CIRCULATORY DISEASE OF THE LOWER LIMBS, IN PARTICULAR FOR APPLYING COMPRESSIVE SUPPORT TO THE LEG AFTER A VENOUS ULCER

This is a Continuation of application Ser. No. 09/202,361 filed Jan. 7, 1999, which is a 371 of PCT/FR97/01067, filed Jun. 13, 1997, the disclosures of which are incorporated herein by reference.

The invention relates to the field of compressive orthoses of the sock type for treating circulatory disease of the lower limbs.

In the present description, the term "orthosis" is used in its conventional medical sense, i.e. an appliance for applying assistance to a region of the body to mitigate a functional deficiency of the locomotive system, and excluding prostheses which are replacement appliances. A "sock" is an orthosis surrounding the leg and the foot, it being understood that the sock may extend upwards, where appropriate, to the knee, to the middle of the thigh, or to the top of the thigh, and that the foot is not necessarily completely covered, and on the contrary it is often preferable for the sock to terminate, e.g. level with the base of the toes.

In the present case, the functional deficiency in question is circulatory deficiency of a lower limb, which deficiency is mitigated by applying compressive support, more particularly support that applied degressive compression, i.e. compression that is applied over all or part of the length of the lower limb starting from the ankle and with the amount of compression decreasing with increasing distance from the ankle.

One of the most common diseases to which the invention is advantageously applicable is treating a venous ulcer or a wound that requires compression. The healing of venous ulcers in the leg necessarily requires appropriate and effective compressive support, with compression being a fundamental part of the treatment.

At present, the vast majority of cases requiring such compression are treated using non-removable elasto-compressive socks (NECS) put into place by the practitioner using adhesive elastic strips which are used once only or dry strips which are washable, but which rapidly lose their initial compressive qualities. The dressing is changed every 3 to 10 days, as a function of the amount of exudate produced by the wound, and the average duration of treatment is about 70 days for a varicose ulcer without complications and of area smaller than 15 cm$^2$.

NECS suffer from numerous drawbacks:
 the skin must be protected by a plain or moss stitch undersock;
 a trained operative is required to put the strip into place, which strip is then left in place for several days;
 the pressure applied to the strip is imprecise, depending a great deal on the skill of the operative;
 troublesome creases in the strip when walking; and
 poor vertical stability of the bandages when walking.

Automatic degressive compression by means of an elastic stocking would be better adapted to such treatment and much more comfortable to patients, while nevertheless being just as effective, therapeutically, as are NECS. However, at present, elastic stockings are used very little for this indication since they are expensive articles. Leg ulcers run a great deal, so the stockings are quickly dirtied and damaged, making the cost of treatment prohibitive since it is always very lengthy, as mentioned above.

An object of the present invention is to remedy that difficultly, by proposing a novel sock-type compressive orthosis (in the sense given above) which satisfies all of the following conditions:
 article for single use;
 article of low cost;
 article easy to handle by a practitioner;
 article of one size only;
 compressive support effective for the particular disease in question;
 compressive support is degressive;
 no compression of the foot;
 readjustment possible without removing the article; and
 compatible with the article being worn continuously, for several days or even several weeks, and in particular when prone (typically at night).

To this end, the orthosis of the invention which is a compressive orthosis of the sock type for treating circulatory diseases of the lower limbs, in particular for providing compressive support to the leg after a venous ulcer, the orthosis being suitable for applying compressive support over all or part of the leg and that is degressive from the ankle, is characterized in that it comprises a knitted compressive tubular portion of varying section constituted by a leg portion of an elastic stocking without a foot or a heel, said compressive tubular portion being extended at its bottom end by a knitted non-compressive tubular portion suitable for covering at least a portion of the foot without compressing it.

According to various advantageous subsidiary characteristics:
 the non-compressive tubular portion has reinforcing yarn in its knitting, over at least a portion of its circumference;
 the non-compressive tubular portion is made using a plain moss type stitch;
 the compressive tubular portion is extended at its top end by another knitted non-compressive tubular portion;
 the orthosis is made in the form of a continuous knitted tube of varying section made of non-run stitch that is alternately compressive and non-compressive, the tube being constituted by a sequence of similar individual elements separable by cutting the tube, each of said elements forming an individual sock extending between two cutting-out zones defining the sock and situated in the regions of non-compressive knitting;
 in which case, in a first implementation, the individual elements form a sequence of elements disposed in opposite directions, each element being the reflection of an adjacent element about axes of symmetry situated in the regions of the cutting-out zones;
 in a second implementation, the individual elements form a sequence of elements disposed the same way round, each element being a copy of an adjacent element representing a shift of a module of length equal to one individual element; and
 the knitting of the tube includes at least one breakable thread in each cutting-out zone.

Other characteristics and advantages of the invention appear on reading the detailed description below.

FIG. 1 is an elevation view from behind of the sock of the invention in the free state, prior to being put on.

FIG. 2 is an elevation view, as seen from one side, of the sock of the invention in place on the leg and the foot of a patient.

FIG. 3 is a view of a continuously knitted tube in a first implementation of the invention.

FIG. 4 shows a second implementation of the invention.

FIG. 5 shows a first possible stitch structure for knitting the tube.

FIG. 6 shows a second possible stitch structure for the knitting.

FIGS. 7 and 8 show two possible variant ways of separating the tube into individual socks.

FIG. 9 shows the texture of the tube in the vicinity of the separation line for the case shown in FIG. 8.

FIGS. 1 and 2 show a sock type orthosis of the invention respectively in the free state (before being put on) and in place on the leg and the foot of a patient.

The sock 1 is essentially constituted by a central portion 2 of compressive stitch of shape and texture corresponding to those of a conventional elastic stocking but having no foot or heel. The length a of this compressive portion varies from one article to another as a function of the size and shape of the patient's leg, and serves as a compressive element that is applied against the dressing of the ulcer.

At its bottom or "distal" end, this compressive portion 2 is extended by a non-compressive portion 3 which is advantageously lacking in a knitted foot or heel, i.e. when in the free state, it constitutes a simple tubular element; its stitch should be of sufficiently stretchable nature to enable it to surround the foot easily without compressing it and without creasing, as shown in FIG. 2.

In the free state, the length b of this non-compressive portion 3 can be b=14 cm, for example, which suffices to cover the major portion of the foot as far as the base of the toes, while avoiding any risk of forming undesirable creases. This portion 3 extends over a length B that varies, being short over the top of the foot and much longer around the back face because of the presence of the heel which it needs to go round.

The top or "proximal" portion of the compressive portion 2 can be extended by another non-compressive portion 4 of relatively short length c, e.g. c=8 cm.

Before being put on, the sock of the invention is thus in the form of a knitted tube of varying section, having a top opening 5 into which the foot is inserted and a bottom opening 6 allowing the end of the foot to poke out freely.

Once in place on the leg 7 and the foot 8 of the patient, the central compressive portion 2 serves to apply compressive support to the leg over a length A that includes the region of the ulcer together with its dressing.

In particular, the structure of the sock of the invention makes it easy to adjust and to readjust the transition line 9 between the compressive portion 2 and the non-compressive portion 3, corresponding to the zone where compression begins (and also to the zone where compression is at its maximum).

The practitioner can thus ensure that the position 11 of the transition line 9 is accurately adjusted, and can also adjust the inclination of this line (arrows 12) so as to be capable of covering all possible situations, particularly for ulcers situated in the region of the malleolus 10, a situation that is quite common. The line 9 can thus be placed beneath the malleolus (covering a portion of the ankle), can pass over the malleolus, or can be situated above it.

The non-compressive bottom portion 3 surrounds and protects the foot over its entire distal region adjacent to the zone of compression. It is important for the distal end of the sock to be open since this configuration enables the practitioner to lift the non-compressive portion 3 easily to inspect the wound visually, to readjust the dressings, etc., without it being necessary to remove the sock.

To accommodate wear of the non-compressive portion 3 in the heel region, it is advantageous to include a non-compressive reinforcing yarn 13 in the moss stitch, e.g. a fairly coarse polyamide yarn. Advantageously, the reinforcement is provided only over a fraction 14 of the circumference of the tube formed by the non-compressive portion 3, e.g. over half said circumference, as shown at 14 in FIG. 1 which is a view of the sock from behind.

The various portions are given their sizes by an appropriate choice of knitting stitch so as to satisfy all of the following criteria in the intended indication:

for the compressive portion 2:
the degree of compression must be sufficient to provide the desired compressive support, but the pressure applied must be less than that which would be applied for reduction of lymphoedema (no attempt is being made to obtain drainage, only to apply compression perpendicularly to the skin);
the compression must be degressive going up from the ankle, and must be effective only from the ankle (unlike lymphoedema reduction where the compression must be applied starting from the toes); and
above all, the foot must not be compressed at all, in the same manner as a conventional elastic stocking where the compression on the foot is practically non-existent, because of the knitted foot and heel;
concerning the elasticity of the stitch, the elastic return force must be compatible with the sock being worn while prone at night, at a time when there is a significant reduction in venous and oncotic pressure; nevertheless, a certain amount of elasticity must be present and appropriate for the size and shape of the patient since the need to wear the article continuously day and night for several days or even several weeks means that it is not possible to use a non-stretch article, nor is it possible to use an article that produces a compressive force that is too great to be acceptable while prone;
the article must be easy to put on a leg that is deformed, having fragile teguments, and on which bulky dressings are applied covering hydrocolloidal plates, which treatment is nowadays recommended for reduction of venous ulcers of the legs; and
it must be possible to readjust the sock and dressings at the ankle, as is made possible in particular by the lack of any knitted foot and by the lack of any pressure exerted on the foot.

The sock of the invention is advantageously fabricated in the form of a continuous knitted "tube" of interconnected individual socks, which are cut apart after fabrication, or subsequently by the practitioner for the purpose of applying them on an ulcer dressing.

In the implementation shown in FIG. 3, the tube 20 is made up of successive socks 1, 2 disposed symmetrically about axes 16 and 17 respectively via the ankle and via the thigh (or knee), i.e. successive socks are interconnected via the ankles and then via the thighs. Each element 1 can be separated to constitute an individual element of length L comprising a compressive leg portion 2 extending between the non-compressive thigh region 4 and the non-compressive ankle region 3.

In a variant, as shown in FIG. 4, the elements 1 can all be the same way round, with a location at each axis 18 where a thigh region 4 is connected to an ankle region 3 of the adjacent sock.

The tube 15 is knitted continuously (and thus at a high rate and at low cost) with varying section so as to match the corresponding leg shape and provide the looked for degressive compression.

The knitting is of conventional type, but it must be a non-run stitch so that it does not run at either end. It is designed to impart degressive compression corresponding to class II or class III in the region of its leg portion 2, which class of compression is particularly suitable for treating venous ulcers. In its non-compressive portions 3 and 4, the stitch may be a plain moss stitch, for example.

The sock can be made of optionally-covered yarn and requires no dying after knitting. Its cost price can be very low and thus compatible with an article for single use.

By way of example, and as shown in FIG. 5, the knitting can be a circular knit with weft filling: reference 19 designates the weft yarn which yarn may optionally be covered and which is elastic in the leg portion 2; while reference 20 designates the knit yarn which may optionally be elastic. This structure is conventional for elastic stockings.

In a variant, the leg portion 2 may have a structure of the support stocking type as shown in FIG. 6, e.g. a structure of the 1×1 micromesh type having a textured or flat elastic yarn 21 and an optionally covered elastic yarn 22, or indeed a plain, alternating float 1×1 micromesh structure, etc.

Whatever the structure selected, the non-elastic yarn can be, for example, flat or textured polyamide type yarn, and the elastic yarn can be covered yarn (traditional covering or Air Jet covering, for example) or bare yarn (elasthane, natural latex, etc.).

To cut up the tube into individual socks, in a first variant as shown in FIG. 7, a pair of scissors is used in the thigh region 4 and in the ankle region 3, possibly together with adjustment for length.

In a variant as shown in FIG. 8, a special meltable or breakable thread 23 (e.g. of the EMS or Luxilon type) can be provided in the separation zones so as to make it easier to separate the various socks. FIG. 9 shows the presence of such a breakable thread 23 in the knitting in the separation zone, with such a thread being provided transversely, e.g. in one or two rows of the tube.

What is claimed is:

1. A compressive orthosis of the sock type for providing compressive support to the leg in the treatment of a venous ulcer, the orthosis being suitable for applying compressive support over all or part of the leg, and that is degressive from the ankle, which orthosis is characterized in that it comprises
   a) a knitted compressive tubular portion of varying section constituted by a leg portion of an elastic stocking without foot or heel, and adapted to apply compressive support to the leg over a length that includes the region of the ulcer together with its dressing, said compressive tubular portion being extended at its bottom end by
   b) a knitted non-compressive portion of tubular form with no foot or heel shape when not being worn and constituted by a stitch sufficiently stretchable to cover at least a portion of the foot to the base of the toes, without compressing the foot and without creasing.

2. The sock type orthosis of claim 1, in which the non-compressive tubular portion has reinforcing yarn in its knitting, over at least a portion of its circumference.

3. The sock type orthosis of claim 1, in which the non-compressive tubular portion is made using a plain moss type stitch.

4. The sock type orthosis of claim 1, in which the compressive tubular portion is extended at its top end by another knitted non-compressive tubular portion.

5. A compressive orthosis of the sock type for treating circulatory diseases of the lower limbs, in particular for providing compressive support to the leg after venous ulcer, the orthosis being suitable for applying compressive support over all or part of the leg, and that is degressive from the ankle, which orthosis is characterized in that it comprises a knitted compressive tubular portion (2) of varying section constituted by a leg portion of an elastic stocking without a foot or a heel, said compressive tubular portion being extended at its bottom end by a knitted non-compressive tubular portion (3) suitable for covering at least a portion of the foot without compressing it, and characterized in that it is made in the form of a continuous knitted tube of varying section made of non-run stitch that is alternately compressive and non-compressive, the tube being constituted by a sequence of similar individual elements (1) separable by cutting the tube, each of said elements forming an individual sock extending between two cutting-out zones defining the sock and situated in the regions of non-compressive knitting.

6. A compressive orthosis of the sock type for providing compressive support to the leg in the treatment of a venous ulcer, the orthosis being suitable for applying compressive support over all or part of the leg, and that is degressive from the ankle, which orthosis is characterized in that it comprises
   a) a knitted compressive tubular portion of varying section constituted by a leg portion of an elastic stocking without foot or heel, and adapted to apply compressive support to the leg over a length that includes the region of the ulcer together with its dressing, said compressive tubular portion being extended at its bottom end by
   b) a knitted non-compressive portion of tubular form with no foot or heel shape when not being worn and constituted by a stitch sufficiently stretchable to cover a portion of the foot at least to the base of the toes to surround and protect the foot over its entire distal region, without compressing the foot and without creasing.

* * * * *